United States Patent
Mark

(10) Patent No.: US 8,688,198 B2
(45) Date of Patent: Apr. 1, 2014

(54) SURGICAL SITE MARKER DELIVERY SYSTEM

(75) Inventor: Joseph L. Mark, Indianapolis, IN (US)

(73) Assignee: Suros Surgical Sytems, Inc., Indianapolis, IN (US)

( * ) Notice: Subject to any disclaimer, the term of this patent is extended or adjusted under 35 U.S.C. 154(b) by 1459 days.

(21) Appl. No.: 11/284,677

(22) Filed: Nov. 22, 2005

(65) Prior Publication Data
US 2007/0118034 A1 May 24, 2007

(51) Int. Cl.
*A61B 17/00* (2006.01)
(52) U.S. Cl.
USPC .......................................... 600/431; 606/116
(58) Field of Classification Search
USPC ................... 606/116, 213, 130; 600/562, 431
See application file for complete search history.

(56) References Cited

U.S. PATENT DOCUMENTS

| | | | |
|---|---|---|---|
| 4,900,304 A * | 2/1990 | Fujioka et al. .................. | 604/60 |
| 4,994,028 A * | 2/1991 | Leonard et al. ................. | 604/60 |
| 5,581,062 A * | 12/1996 | Gomez, Jr. .................. | 200/84 C |
| 5,782,775 A * | 7/1998 | Milliman et al. ............. | 600/567 |
| 5,879,357 A * | 3/1999 | Heaton et al. ................. | 606/116 |
| 5,902,310 A | 5/1999 | Foerster et al. | |
| 6,056,700 A * | 5/2000 | Burney et al. ................. | 600/564 |
| 6,261,243 B1 * | 7/2001 | Burney et al. ................. | 600/564 |
| 6,371,904 B1 * | 4/2002 | Sirimanne et al. ................. | 600/3 |
| 6,494,892 B1 * | 12/2002 | Ireland et al. ................. | 606/180 |
| 6,972,022 B1 * | 12/2005 | Griffin .......................... | 606/116 |
| 7,001,341 B2 * | 2/2006 | Gellman et al. .............. | 600/562 |
| 7,083,576 B2 * | 8/2006 | Zarins et al. .................. | 600/562 |
| 2003/0028178 A1 * | 2/2003 | Chin ................................. | 606/1 |
| 2003/0114797 A1 * | 6/2003 | Vaillancourt et al. ......... | 604/171 |
| 2003/0204137 A1 * | 10/2003 | Chesbrough et al. ......... | 600/426 |
| 2003/0233101 A1 * | 12/2003 | Lubock et al. ................ | 606/116 |
| 2004/0077938 A1 * | 4/2004 | Mark et al. .................... | 600/411 |
| 2004/0097981 A1 | 5/2004 | Selis | |
| 2004/0127987 A1 * | 7/2004 | Evans et al. ................. | 623/11.11 |
| 2004/0230133 A1 * | 11/2004 | Miller et al. .................. | 600/562 |
| 2004/0236211 A1 * | 11/2004 | Burbank et al. .............. | 600/431 |
| 2005/0085842 A1 * | 4/2005 | Eversull et al. ............... | 606/191 |
| 2005/0119562 A1 * | 6/2005 | Jones et al. .................... | 600/426 |
| 2005/0222614 A1 * | 10/2005 | Ginn et al. .................... | 606/213 |
| 2005/0277871 A1 | 12/2005 | Selis | |

(Continued)

FOREIGN PATENT DOCUMENTS

WO WO-9717103 A 5/1997
WO WO 03/022133 A2 * 3/2003

(Continued)

OTHER PUBLICATIONS

PCT International Search Reported #PCT/IB2006/054259 dated Aug. 9, 2007.

*Primary Examiner* — Kathleen Holwerda
*Assistant Examiner* — Sarah Simpson
(74) *Attorney, Agent, or Firm* — Vista IP Law Group LLP

(57) ABSTRACT

A site marker delivery system is provided. The site mark delivery system includes an outer cannula having an open distal end. The outer cannula defines an inner lumen in which an inner cannula may be received. A marker is also positioned within the inner lumen of the outer cannula. The inner cannula further includes a trigger mechanism that when actuated injects the marker through the open distal end of the outer cannula into a biopsy site.

9 Claims, 8 Drawing Sheets

(56) References Cited

U.S. PATENT DOCUMENTS

| | | | |
|---|---|---|---|
| 2006/0084886 A1* | 4/2006 | Reydel | 600/564 |
| 2006/0129062 A1* | 6/2006 | Nicoson et al. | 600/566 |
| 2006/0135981 A1* | 6/2006 | Lenker et al. | 606/191 |
| 2006/0155209 A1* | 7/2006 | Miller et al. | 600/566 |
| 2006/0200189 A1* | 9/2006 | Nance et al. | 606/198 |
| 2006/0260994 A1* | 11/2006 | Mark et al. | 210/232 |
| 2007/0010843 A1* | 1/2007 | Green | 606/185 |
| 2007/0016017 A1* | 1/2007 | Mark et al. | 600/431 |
| 2007/0123800 A1* | 5/2007 | Nishtala et al. | 600/567 |
| 2007/0142725 A1* | 6/2007 | Hardin et al. | 600/431 |

FOREIGN PATENT DOCUMENTS

| | | | | |
|---|---|---|---|---|
| WO | WO-03022133 A2 | 3/2003 | | |
| WO | WO-2004/012600 | 2/2004 | | |
| WO | WO 2004/084738 A | * 10/2004 | | A61B 10/00 |
| WO | WO-2004084738 A | 10/2004 | | |
| WO | WO-2005063126 A | 7/2005 | | |

* cited by examiner

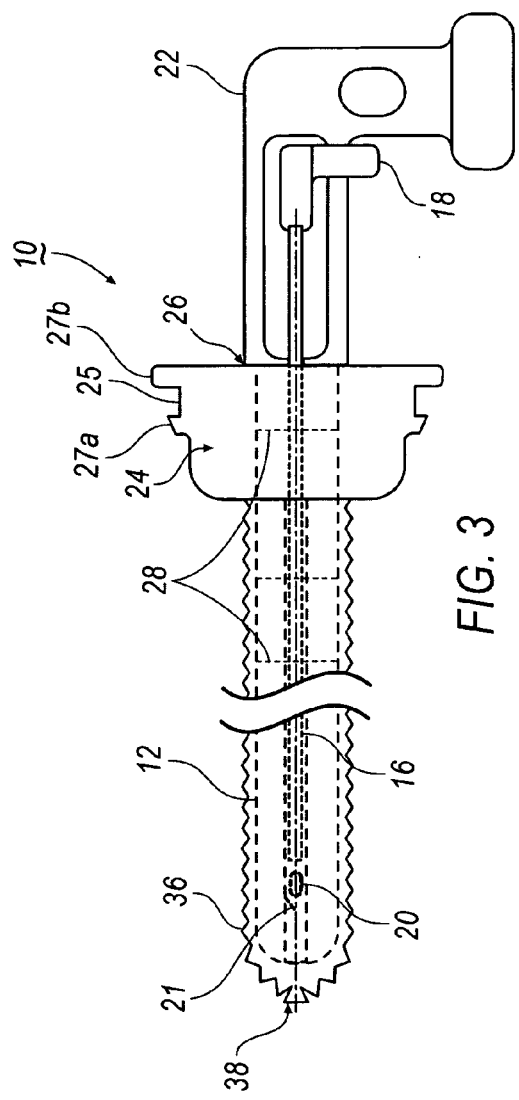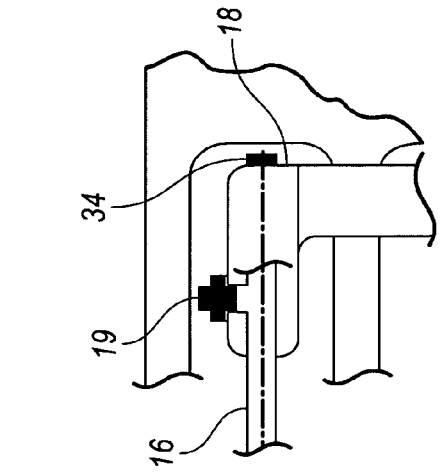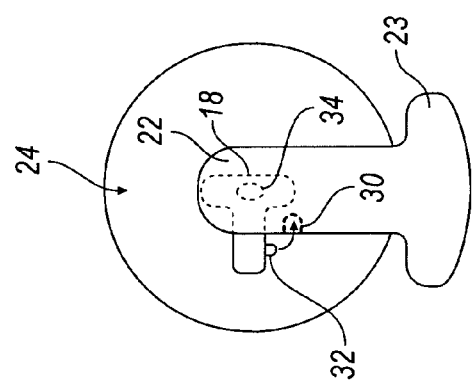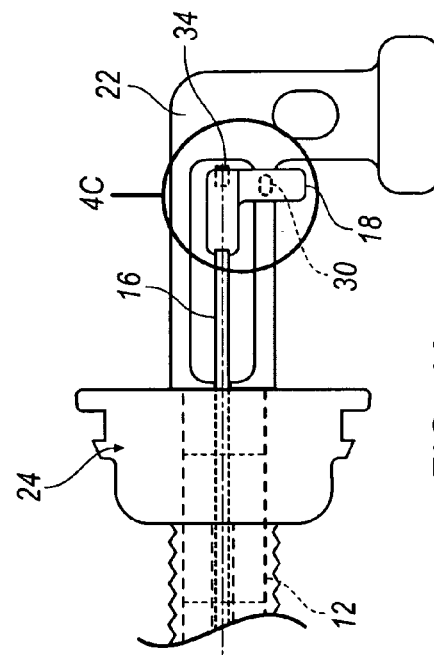

SURGICAL SITE MARKER DELIVERY SYSTEM

FIELD OF THE INVENTION

The invention generally relates to a biopsy site marker delivery system. More particularly, the invention relates to a biopsy site marker delivery system for non-surgically implanting a site marker at a biopsy site after a tissue cutting device is removed from the biopsy site.

BACKGROUND OF THE INVENTION

In the field of breast cancer, stereotactically guided and percutaneous biopsy procedures have increased in frequency as well as in accuracy as modern imaging techniques allow the physician to locate lesions with ever increasing precision. However, for a given biopsy procedure, a subsequent examination of the biopsy site is very often desirable.

For example, in those cases where the lesion is found to be benign, a follow-up examination of the biopsy site may be conducted at a later time. Where the lesion is found to be malignant, the physician may want to place additional site markers to help guide the surgeon to the malignancy.

A number of procedures and devices for marking and locating particular tissue locations are known in the prior art. For example, location wire guides are well known for locating lesions, particularly in the breast. One such known device includes a tubular introducer needle and an attached wire guide, which has at its distal end, a helical coil configuration for locking into position about the targeted lesion. The needle is introduced into the breast and guided to the lesion site using an imaging system of a known type, for example, X-Ray, ultrasound or magnetic resonance imaging (MRI), at which time the helical coil at the distant end is deployed about the lesion. Then, the needle may be removed from the wire guide, which remains locked in position distally about the lesion for guiding a surgeon down the wire to the lesion site during subsequent surgery. While such a location system is effective, it is obviously intended and designed to be only temporary, and is removed once the surgery or other procedure has been completed.

It is also known to employ biocompatible dyes or stains to mark breast lesions. First, a syringe containing the colorant is guided to the detection lesion, using an imaging system. Later, during the extraction procedure, the surgeon harvests a tissue sample from the stained tissue. However, while such staining techniques can be effective, it is difficult to precisely localize the stain. Also, the stains are difficult to detect fluoroscopically and may not always be permanent.

Additionally, it is known to implant markers directly into a patient's body using an invasive surgical technique. This enables a practitioner to later return to the site of the graft by identifying the rings, for evaluation purposes.

Each of the above systems and methods for marking a biopsy site has disadvantages associated with effectiveness, accuracy, and invasive surgical techniques. Accordingly, what is needed is a site marker delivery system for delivering a marker to a biopsy site, and deploying the marker at the site effectively, accurately, and without the need for additional invasive surgical procedures.

SUMMARY OF THE INVENTION

A site marker delivery system is disclosed. The site marker delivery system includes an outer cannula having an open distal end. The outer cannula defines an inner lumen that is sized to receive an inner cannula therewithin. A marker is positioned within the outer cannula and is delivered by the inner cannula at a predetermined biopsy site by a trigger mechanism that is connected to the inner cannula.

The site marker delivery system may be used with a stereotactic biopsy system that includes an adapter assembly for supporting the site marker delivery apparatus. In such a case, the site marker delivery apparatus may include a grommet mounted on the outer cannula is configured to support the outer cannula at a selected longitudinal portion thereof. The grommet is supportable by the adapter assembly in a fixed longitudinal position relative thereto. Fixing the grommet to the adapter assembly maintains the open end of the outer cannula in a predetermined position relative to a distal end of the adapter assembly. Alternatively, the site marker delivery system may also be used with an introducer system or may be a handheld device.

In another embodiment of the marker delivery apparatus, a collapsible sheath may be provided. The collapsible sheath is disposed about the outer cannula. The collapsible sheath is configured to protect the outer cannula from contamination.

BRIEF DESCRIPTION OF THE DRAWINGS

FIG. 3 illustrates a side view of the embodiment of the site marker delivery system of FIG. 2.

FIG. 4A illustrates a fragmented side view of the embodiment of the site marker delivery system of FIG. 2.

FIG. 4B illustrates an end view of the embodiment of the site marker delivery system of FIG. 2.

FIG. 4C illustrates an enlarged view of an optional port formed in an inner cannula of the site marker delivery system of FIG. 2.

DETAILED DESCRIPTION OF THE INVENTION

Figure 1:
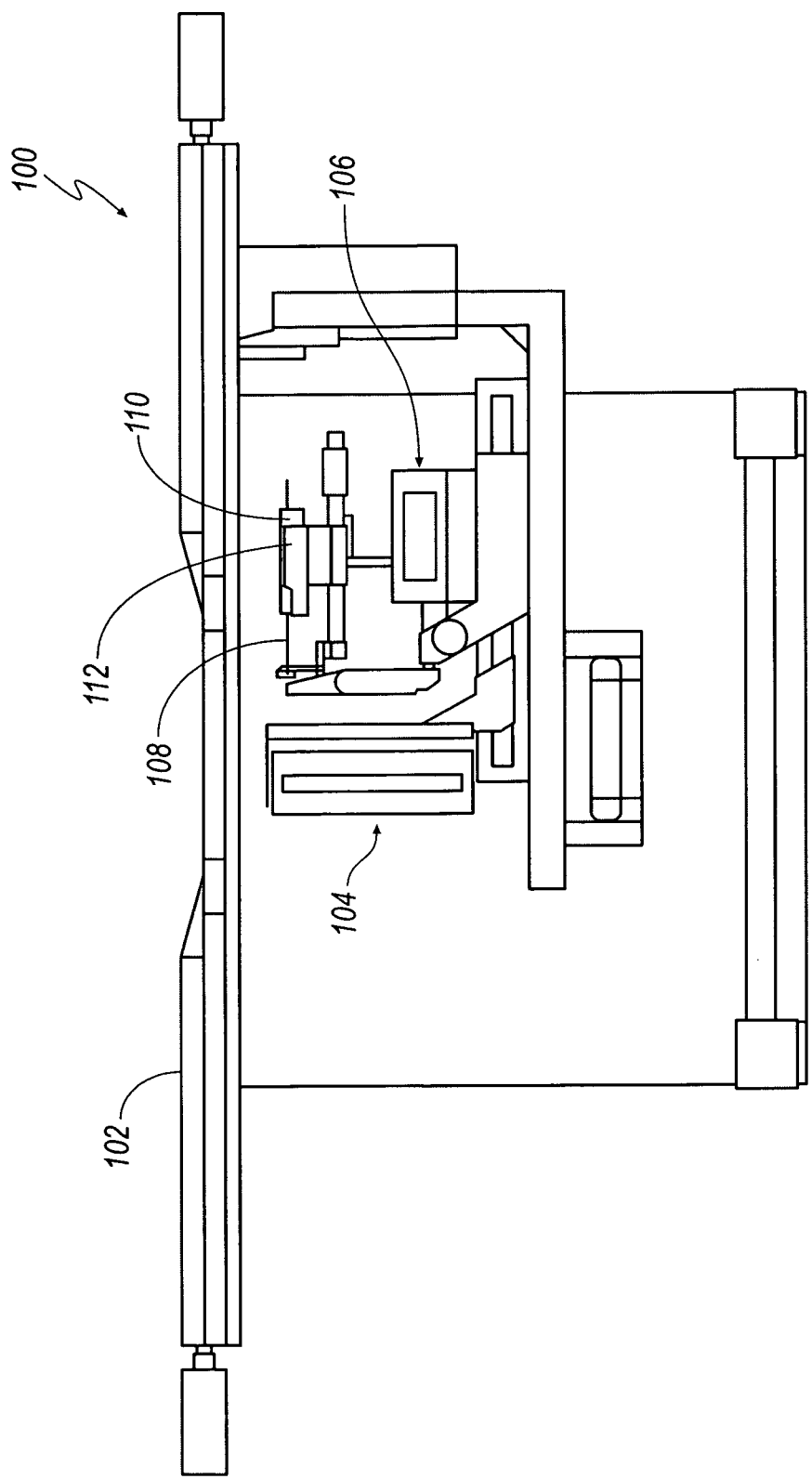
FIG. 1 illustrates a side view of a stereotactic biopsy system having adapter assembly for supporting a site marker delivery apparatus.

Referring now to the drawings, preferred embodiments of the present invention are shown in detail. Although the drawings represent embodiments of the present invention, the drawings are not necessarily to scale and certain features may be exaggerated to better illustrate and explain the present invention. The embodiments set forth herein are not intended to be exhaustive or otherwise limit the invention to the precise forms disclosed in the following detailed description.

The embodiments of the site marker delivery apparatus may be used with a stereotactic biopsy system. Referring to FIG. 1, a simplified illustration of an exemplary stereotactic biopsy system 100 for use in performing minimally invasive, fine-needle aspiration and needle core biopsies of the human breast to determine whether a breast lesion is benign or malignant. The stereotatic breast biopsy system 100 includes an ergonomically contoured table 102 that comfortably supports a patient (not shown) in a stable and fixed position that exposes the patient's breast. The stereotatic breast biopsy system 100 further includes a diagnostic imaging system 104 for targeting the lesion to biopsied. The imaging system 104 provides a location of the target lesion for a guidance system 106 to guide insertion of a biopsy needle 108 into the patient. The biopsy needle 108 is a component of a biopsy device 110 that is supported by the guidance system 106 in an adapter 112. Details of one embodiment of an adapter assembly 112 may be found in U.S. patent application Ser. No. 10/803,698 entitled, "Adapter Assembly for Stereotactic Biopsy" filed on Mar. 18, 2004, the disclosure of which is hereby incorporated by reference in its entirety. After the target lesion is biopsied, the biopsy device 110 is removed from the adapter and a site marker delivery apparatus may be placed thereon.

While one exemplary stereotatic breast biopsy system has been shown, it is understood that the present invention may be used with other known breast biopsy systems, such as the Mammotone system manufactured by Johnson & Johnson, and the ATEC® manufactured by Suros. Further, the breast biopsy system used with the embodiments of the present invention may be either front loaded systems, or rear loaded systems.

Figure 2:
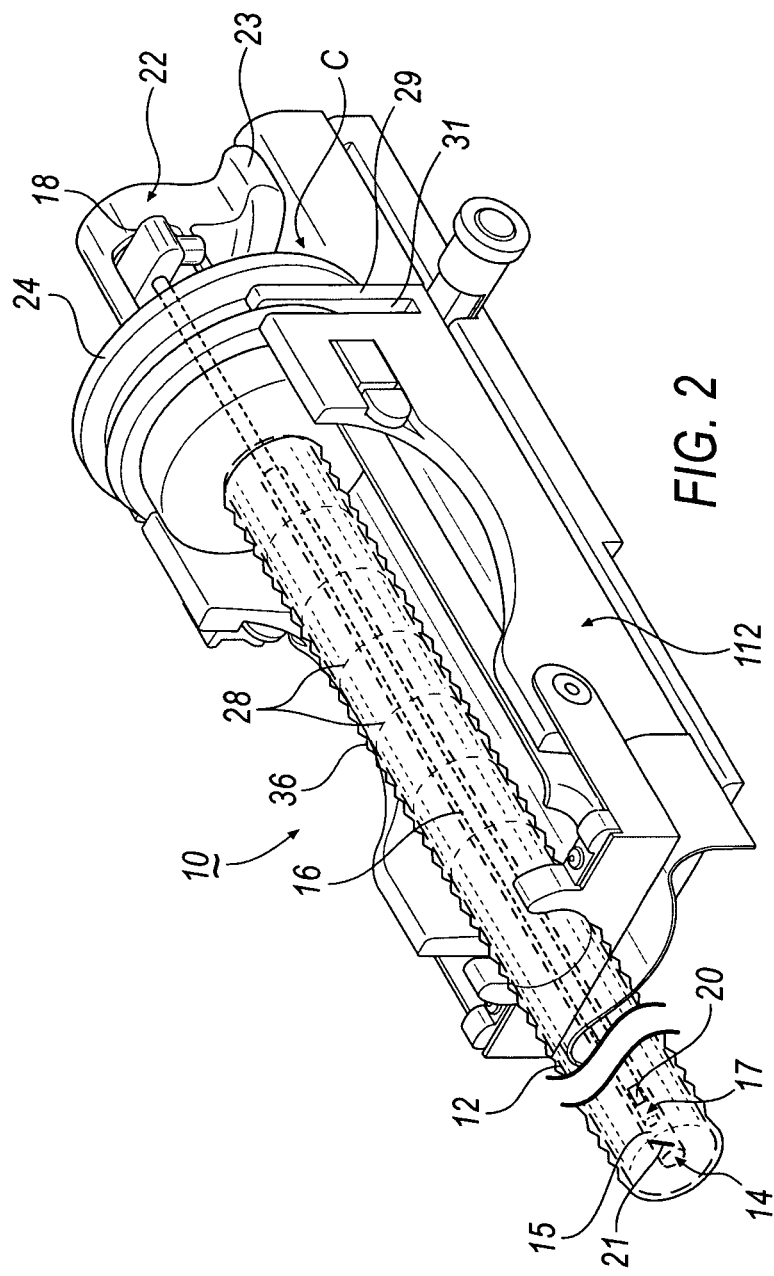
FIG. 2 illustrates a perspective view of an embodiment of a site marker delivery system mounted on an adapter assembly.

FIG. 2 illustrates an embodiment of a site marker delivery system 10 configured for efficiently, accurately and sanitarily depositing a marker at a biopsy site. The marker delivery system 10 includes advantages over conventional delivery devices which are sometimes difficult to use, often result in inaccurate placement of a marker within the biopsy cavity.

While the site marker delivery system 10 may be constructed of any suitable material, it is preferred that site marker delivery system 10 is constructed of medical grade materials, for example, stainless steel, plastic and rubber. Other advantages provided by the site marker delivery system 10 over conventional marker delivery devices will become apparent from reading the following.

FIGS. 2 and 3 illustrate the details of an embodiment of a site marker delivery system 10. Site marker delivery system 10 includes an outer cannula 12 open at a distal end 14 thereof. The outer cannula includes an inner lumen 15 (shown in phantom) dimensioned so as to slidably receive an inner cannula 16 (shown in phantom) therein. The inner cannula 16 preferably includes a trigger mechanism 18 that causes the inner cannula 16 to inject a marker 20 (shown in phantom) into a predetermined biopsy site when actuated. The inner cannula 16 may further include a port 17 formed therein that permits injection of a hemostatic agent or other fluids into the biopsy site. While port 17 is shown as being formed in a top surface of trigger mechanism 18, the invention is not limited to this particular configuration. A removable plug 19 may also be included to selectively close port 17 when not in use (FIG. 4C). The outer cannula 12 may further include a one-way flap 21 positioned adjacent distal end 14. The flap 21 opens toward distal end 14, only and is configured to prevent the marker 20 from receding back into the inner cannula 16 after injection into the biopsy site.

In one embodiment of the site marker delivery system 10, the outer cannula 12 may further include a number of markings or indicators 28 disposed between the distal 14 and proximal 26 ends at predetermined intervals of discrete lengths. The markings 28 may be used for visually confirming the length of the outer cannula 12 such that the operator oft the site marker delivery system 10 may be selectively adjust the depth of the site marker delivery system 10 when injecting a site marker 20 in a manner further described below.

The outer cannula 12 may be fixedly attached to a handpiece 22 at the proximal end 26 thereof. The handpiece 22 allows convenient holding and manipulation of the site marker delivery system 10. In one embodiment, the handpiece 22 includes a proximal end 23 that has an outer contoured surface that is complementary to a surface of the C of an adapter assembly 112 (as best seen in FIG. 2. The cooperating surfaces of proximal end 23 and adapter assembly 122 to enhance the stability of the site marker delivery system 10 when mounted thereon.

In one embodiment, a grommet 24 is mounted around the outer cannula 12 adjacent the proximal end 26 thereof. The grommet 24 may include one or more grooves 25 defined by annular flanges 27a, 27b that are configured to support the outer cannula 12 at a selected longitudinal portion thereof (as best seen in FIG. 3). For example, when site marker delivery system 10 is being supported on the adapter assembly 112, adapter assembly 112 may include a mounting projection 29 and mounting groove 31 (best seen in FIG. 2). Flange 27a engages mounting groove 29 and flange 27b is positioned against an outside surface of mounting projection 29 such that mounting projection 29 is received within groove 25 of grommet 24. Accordingly, the grommet 24 is adapted to be supportable on the adapter assembly 112 at a fixed longitudinal relative thereto. In one embodiment, the grommet 24 is slidably mounted on the outer cannula 12 whereby the grommet 24 can be adjusted to a desired longitudinal position between the proximal 26 and distal 14 ends thereof. For example, after releasably fixing the grommet 24 to the adapter assembly 112, the handpiece 22 can be used to adjust the position of the grommet 24 on the outer cannula 12 by pulling (or pushing) the handpiece 22 until the grommet 24 aligns with one of the number of markings 28 on the outer cannula 12 (See FIG. 5). This allows an operator to adjust the working length of the outer cannula 12 such that the distal end 14 thereof can be accurately positioned at the biopsy site for depositing the marker 20. The working length of the outer cannula 12 is considered to be the portion thereof that will be inserted into the patient such that the distal end 14 of the outer cannula 12 is positioned at the biopsy site.

Figure 2A:
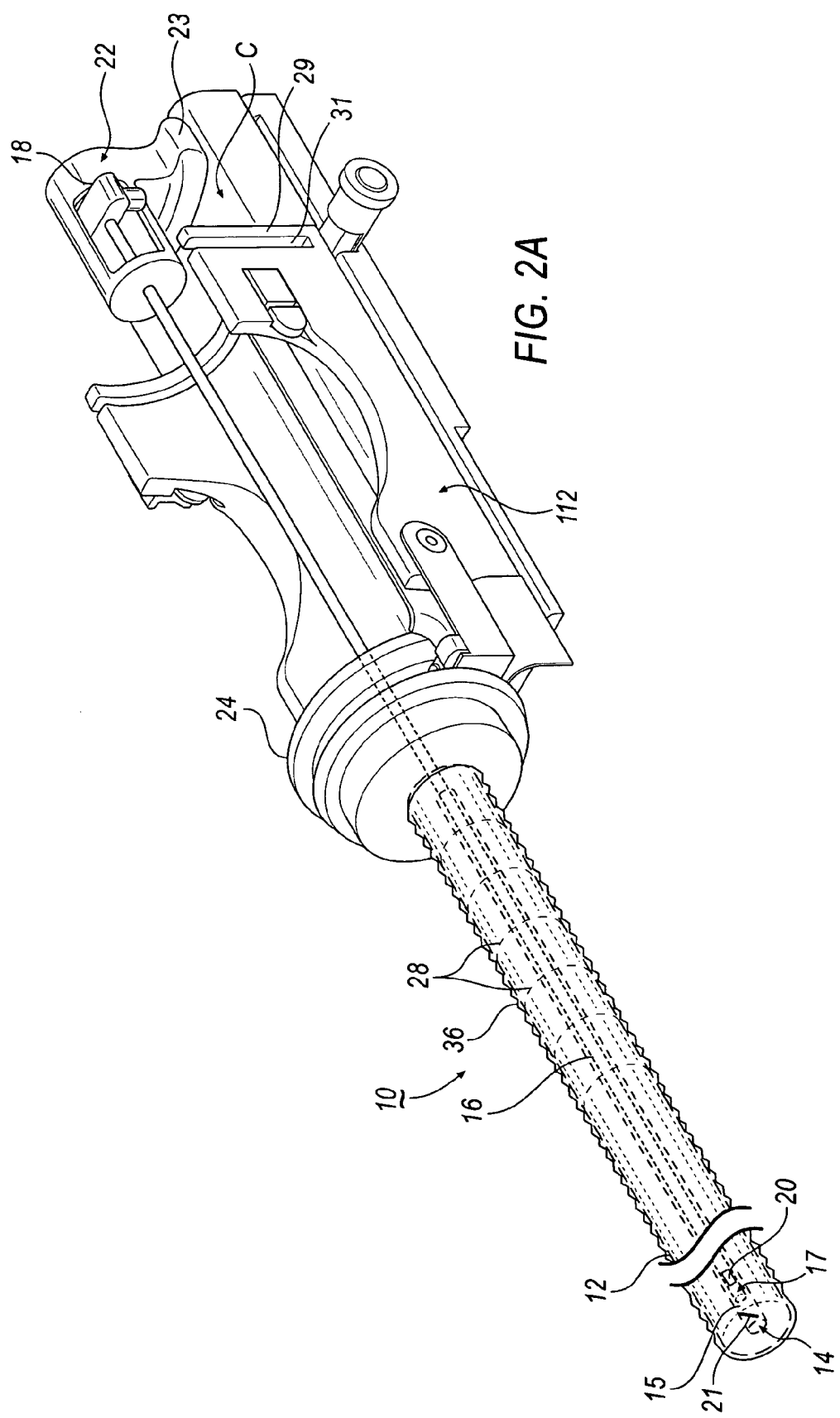
FIG. 2A illustrates a perspective view of an alternative embodiment of a site marker delivery system mounted on an adapter assembly.

In an alternative embodiment, as shown in FIG. 2A, grommet 24 is positioned adjacent a forward end of adapter assembly 112. Positioning grommet 24 in this location will shorten the working length of outer cannula 12.

FIGS. 4A and 4B illustrate a fragmented side view and a proximal end view of the site marker delivery system 10. In one embodiment, the handpiece 22 is provided with a notch or aperture 30 formed in an outer surface there of that is configured to receive a corresponding projection 32 formed on an outer surface of the trigger mechanism 18. When engaged, the notch 30 and projection 32 cooperate to lock the inner cannula 16 in position. Thus, if the handpiece 22 is used to adjust the longitudinal position of the outer cannula 12 then the inner cannula 16 will move likewise whereby the relative position between the outer 12 and inner 16 cannula remains constant. Also, the notch 30 and projection 32 keep the inner cannula 16 from moving when a fire button 34 on the trigger mechanism 18 is actuated. It is appreciated that other marker deployment mechanisms may be used with the site marker delivery system 10, without exceeding the scope of the invention disclosed herein.

FIGS. 2-5 also illustrate an optional collapsible sheath 36 disposed over and about the outer cannula 12. The collapsible sheath 36 includes an open distal end 38 which may be bound by an elastic material 40 to urge the distal end 38 substantially closed such that the distal end 14 of the outer cannula 12 is substantially unexposed prior to using the site marker delivery apparatus 10 (best seen in FIG. 3). The collapsible sheath 36 is configured to reduce the risk of contaminating the outer cannula 12 prior to insertion into the biopsy site. A proximal end 42 of the collapsible sheath 36 is preferably configured to move with the grommet 24. Thus, the proximal end 42 may be mechanically fixed to the grommet 24, attached using an adhesive material or other suitable method of securing proximal end 42 to the grommet 24. The collapsible sheath 36 is preferably formed of medical grade flexible material which provides a sterile and protective covering for the outer cannula 12. The material for collapsible sheath 36 may also be partially see-through such that markings 28 on outer cannula may be visible to an operator.

Figure 5:
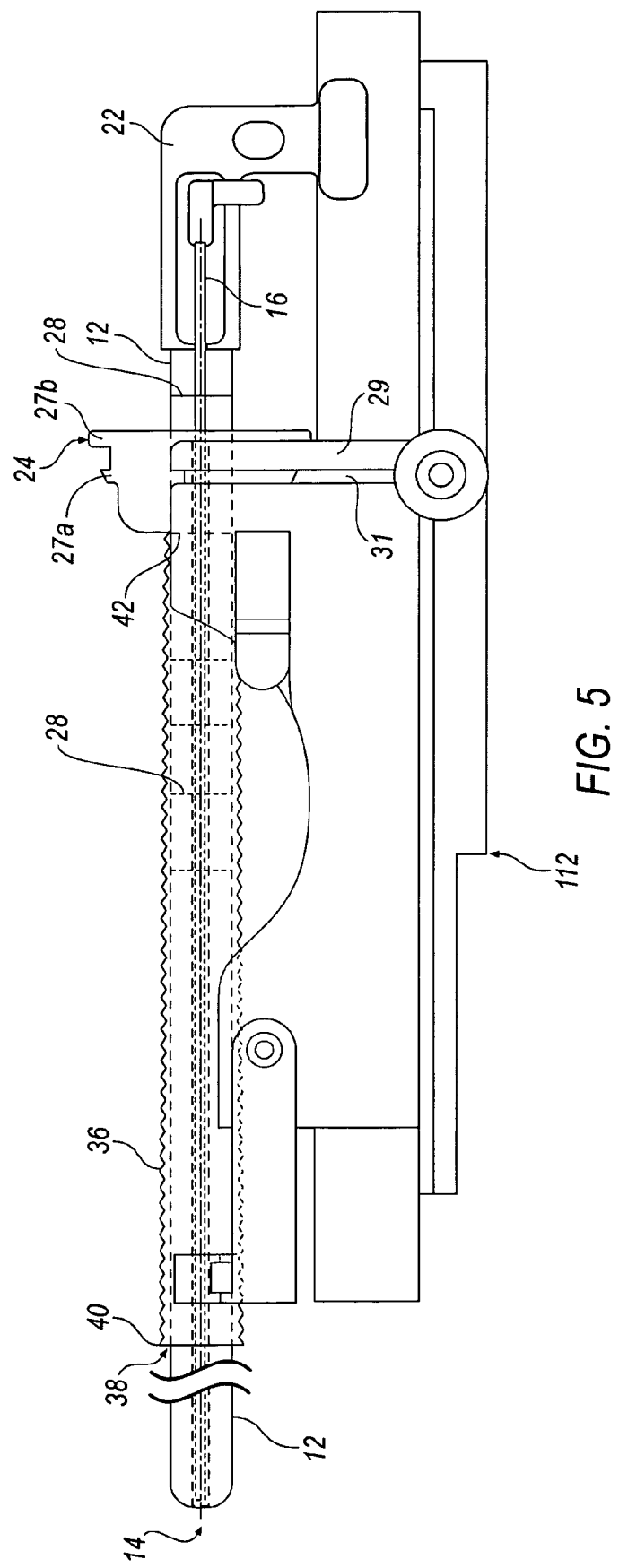
FIG. 5 illustrates a side view of the embodiment of the site marker delivery system of FIG. 2 mounted on an adapter assembly.

Referring to FIG. 5, the collapsible sheath is illustrated partially collapsed such that the outer cannula 12 is exposed. The collapsible sheath 36 is configured to progressively collapse during insertion of the outer cannula 12 into the biopsy site such that any uninserted portion of the outer cannula 12 remains covered by the collapsible sheath 36. FIG. 5 also illustrates grommet 24 in an adjusted position inboard of proximal end 28 such that the working length of the outer cannula 12 is shortened. A number of exposed markings 28 (shown in phantom) indicate that the grommet 24 position on the outer cannula 12 is adjusted from a starting position at proximal end 28. The spacing between the markings 28 preferably correspond to a predetermined distance whereby the user can accurately adjust the working length of the outer cannula 12 to be substantially equal to the distance between the insertion point site marker delivery system 10 and the biopsy site.

Figure 6:
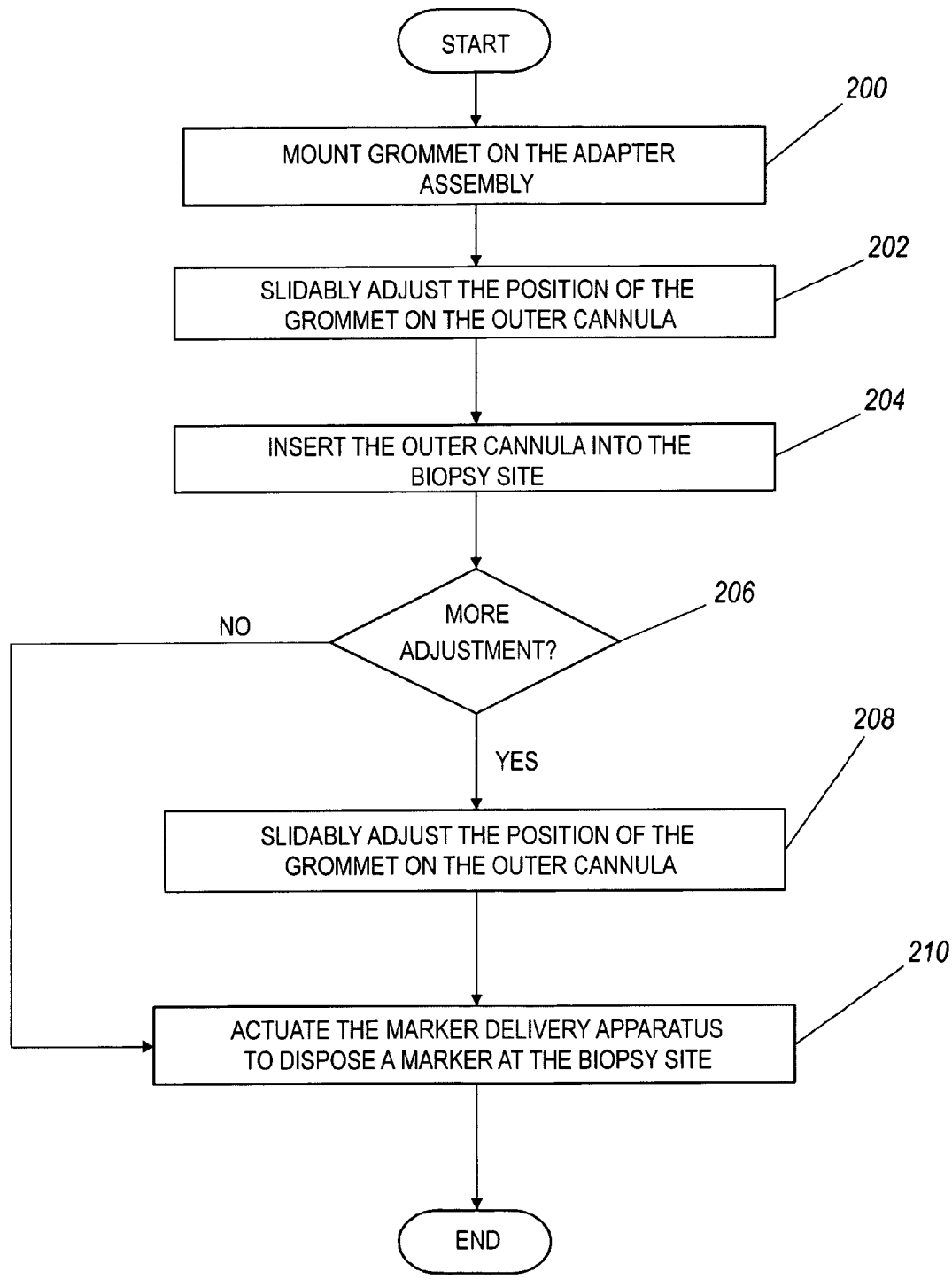
FIG. 6 illustrates a method of using an embodiment of the site marker delivery system.

FIG. 6 illustrates a method for using an embodiment of the site marker delivery system 10 with an adapter assembly, as described herein. At step 200, the grommet 24 of the site marker delivery system 10 is mounted to the adapter assembly 112 of a stereotactic biopsy system. At step 102, the grommet 24 is slidably adjusted on the outer cannula 12 such that the working length of the outer cannula 12 is substantially equal to the distance between the insertion point and the biopsy site. Next, at step 104, the outer cannula 12 is inserted into the biopsy site. The operator then verifies whether further adjustment of the outer cannula 12 is necessary at step 106. This verification is needed to ascertain if further adjustment of the outer cannula 12 is required to accurately position the distal end 14 of the outer cannula 12 at the biopsy site. If so, then the method advances to step 108 where further adjustment is made. If not, then the method advances to step 110. At step 110, the site marker delivery system is actuated to deposit a marker 20 at the biopsy site.

While the method above has been described with respect to use of the site marker delivery system 10 with an adapter assembly 112, use of the site marker delivery system 10 is not limited to use of an adapter assembly 112 for a stereotatic biopsy system. For example, the site marker delivery system 10 may be a handheld unit whereby an operator holds the device in its hand while operating the device. In another embodiment, the site marker delivery system 10 may be utilized with an introducer system.

Figure 7A:
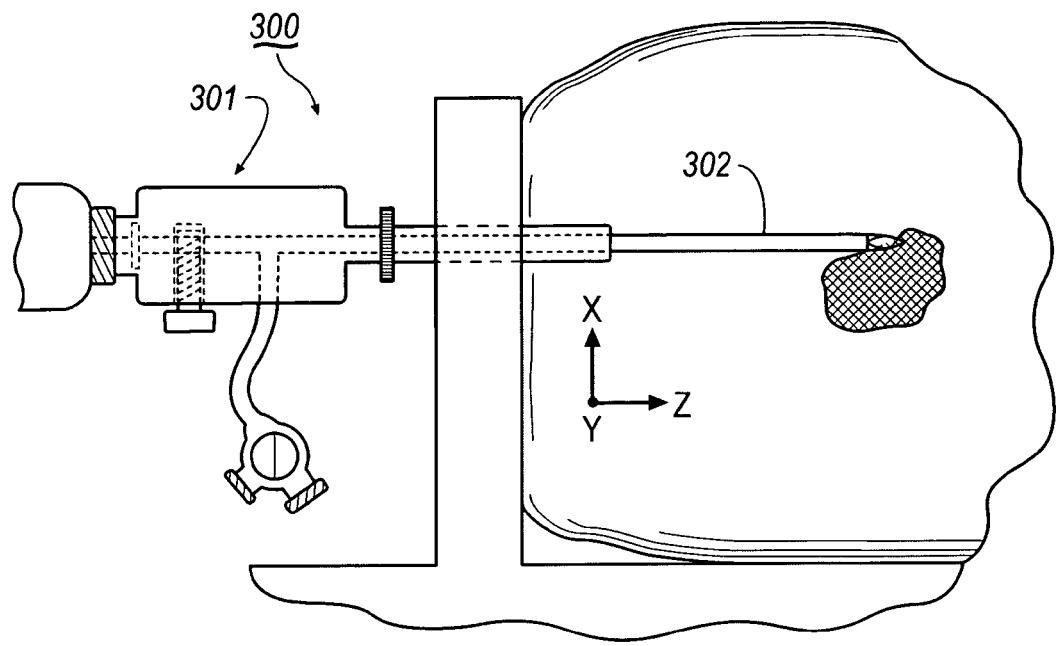
FIG. 7a-7c illustrates a side view of an introducer system for use with an embodiment of the site marker delivery system.
Figure 7B:
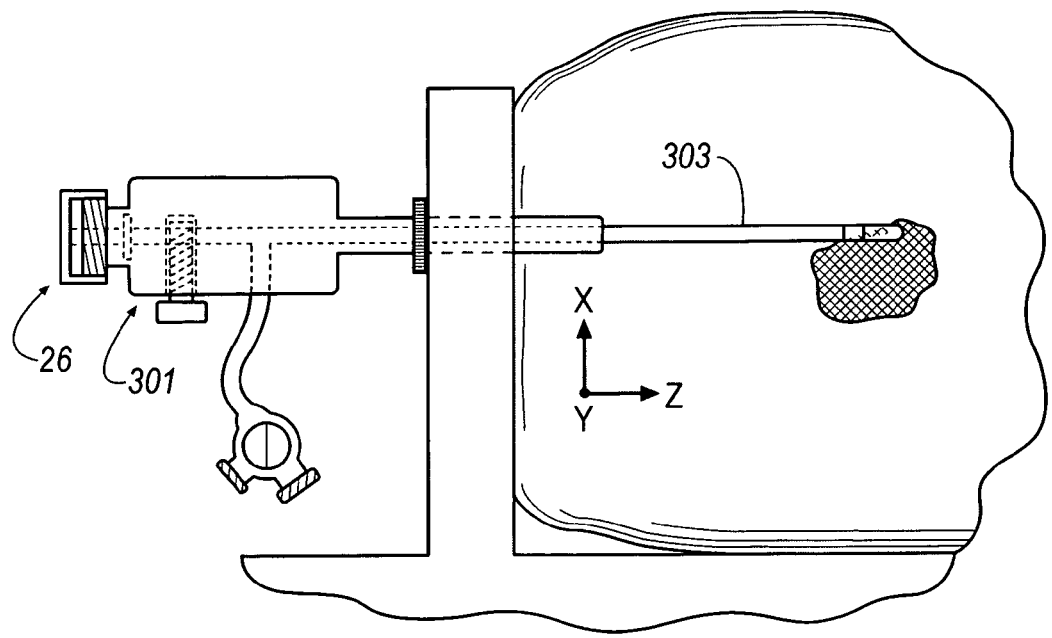
Figure 7C:
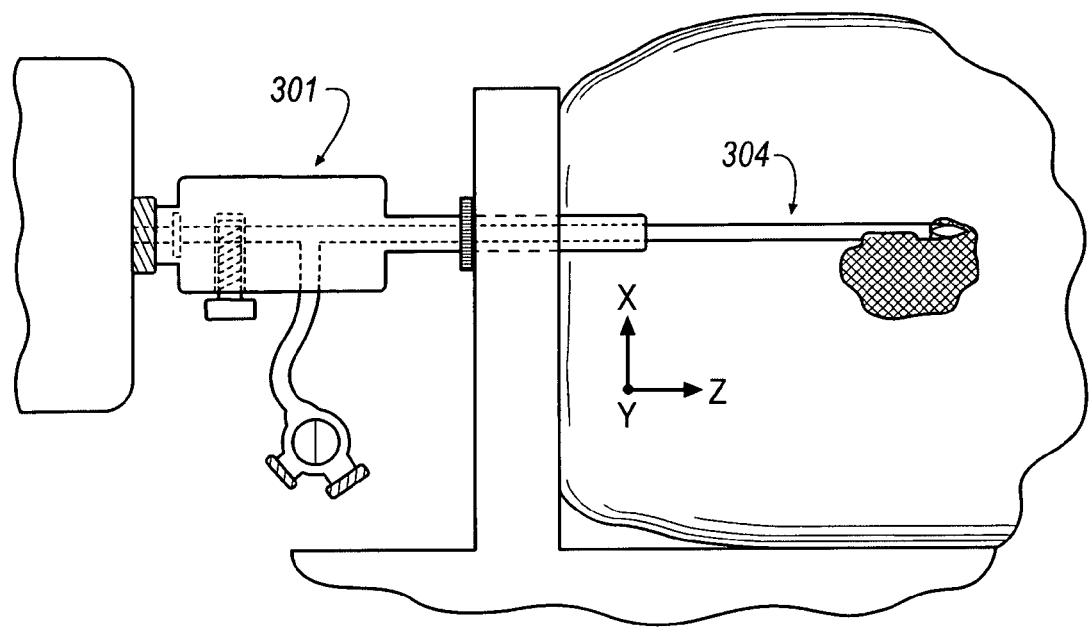

An example of an introducer system is described in co-pending U.S. patent application Ser. No. 10/649,068 entitled, "Introduction System for Minimally Invasive Surgical Instruments" filed on Aug. 27, 2003, the disclosure of which is hereby incorporated by reference in its entirety, as well as shown in FIGS. 7a-7c. The introducer system 300 includes a cannula 301, an introducer stylet 302 removably disposed within the cannula 301, and a target confirmation device 303 that is selectively insertable within the cannula 301. The cannula 301 is sized to fit over the introducer stylet 302 and is positionable at least partially within a patient's body after insertion and removable of the introducer stylet 302. The target confirmation device 303 is insertable into the cannula 301 after removal of the introducer stylet and is configured to confirm the position of the cannula relative to the target biopsy site. Once the target biopsy site is confirmed, a biopsy device 304 may be inserted into the cannula 301 and delivered to the target biopsy site. After a tissue sample is biopsied by the biopsy device 304, the biopsy device 304 may be removed and the site marker delivery system 10 may be inserted through the cannula 301 with the distal end 14 of outer cannula 12 being delivered to the biopsy site. Once positioned, the trigger 18 of site marker delivery system 10 may be deployed to inject a marker 20 into the biopsy site for later evaluation.

The foregoing embodiment of the site marker delivery apparatus is disclosed for illustrative purposes. Many adaptations and modifications will become apparent to one of ordinary skill in the art upon reading the above descriptions. The scope of the invention should be determined with reference to the appended claims, along with the full scope of equivalence to which such claims are entitled.

I claim:

1. A site marker delivery system comprising:
an outer cannula having an open distal end and a proximal end, said outer cannula defining an inner lumen for receiving at least one marker moveably positionable within said inner lumen at a first position;
an inner cannula that is selectively positionable within said inner lumen of said outer cannula, said inner cannula including a distal end and a proximal end;
an actuation mechanism connected to said inner cannula for selectively moving said inner cannula into temporary engagement with said marker while said marker is positioned at said first position within said inner lumen, said actuation mechanism operable for moving said marker from said first position through said open distal end of said outer cannula to a second position external of said inner lumen; and
a grommet slidably attached to said outer cannula, wherein said inner cannula is moveable axially relative to said grommet and said outer cannula is moveably axially relative to said grommet through application of an axial force to said outer cannula.

2. The delivery system of claim 1 further comprising a collapsible sheath disposed about said outer cannula, said collapsible sheath includes an open distal end and a proximal end fixed to a predetermined portion of said outer cannula, said open distal end of the collapsible sheath includes elastic for biasing said open distal end of the collapsible sheath into a normally closed configuration.

3. The delivery system of claim 1, wherein the outer cannula further comprises a one way movable flap formed therein and disposed proximate said distal end.

4. The delivery system of claim 1, wherein said grommet is configured to be mounted to a stereotactic adapter assembly in a fixed longitudinal position relative thereto, said grommet serving to maintain said distal end of said outer cannula at a predetermined position relative to a distal end of the adapter assembly.

5. The delivery system of claim 4, wherein said inner cannula is moveable relative to said adapter assembly and said grommet while said outer cannula is maintained in a fixed position relative to said adapter assembly by said grommet.

6. The delivery system of claim 4, wherein said grommet is maintained in a fixed position relative to said adapter assembly when mounted to said adapter assembly, and said outer cannula is selectively positionable relative to said adapter assembly through the application of said axial force to said outer cannula.

7. The delivery system of claim 1, wherein said site marker delivery system is received at least partially within a cannula of an introducer system.

8. The delivery system if claim 1, wherein said inner cannula further includes a port for selective delivery of fluids to the biopsy site.

9. The delivery system of claim 1, wherein said grommet engages an outer circumference of said outer cannula.

* * * * *